US00PP23501P2

(12) United States Plant Patent
Hammett

(10) Patent No.: US PP23,501 P2
(45) Date of Patent: Mar. 26, 2013

(54) ***DAHLIA* PLANT NAMED 'MYSTIC HAZE'**

(50) Latin Name: *Dahlia variabilis*
Varietal Denomination: Mystic Haze

(76) Inventor: Keith Hammett, Auckland (NZ)

( * ) Notice: Subject to any disclaimer, the term of this patent is extended or adjusted under 35 U.S.C. 154(b) by 0 days.

(21) Appl. No.: 13/317,201

(22) Filed: Oct. 11, 2011

Related U.S. Application Data

(60) Provisional application No. 61/455,188, filed on Oct. 18, 2010.

(51) Int. Cl.
*A01H 5/00* (2006.01)

(52) U.S. Cl. ..... Plt./321

(58) Field of Classification Search ..... Plt./321
See application file for complete search history.

*Primary Examiner* — Annette Para

(57) ABSTRACT

A new cultivar of *Dahlia* named 'MYSTIC HAZE' that is distinguishable by a compact rounded habit, fragrant apricot-orange flowers with a soft yellow inner halo and dark central discs, glossy mahogany-black foliage and dark purple-brown stems. In combination these traits set 'MYSTIC HAZE' apart from all other existing varieties of *Dahlia* known to the inventor.

2 Drawing Sheets

Figure 1:
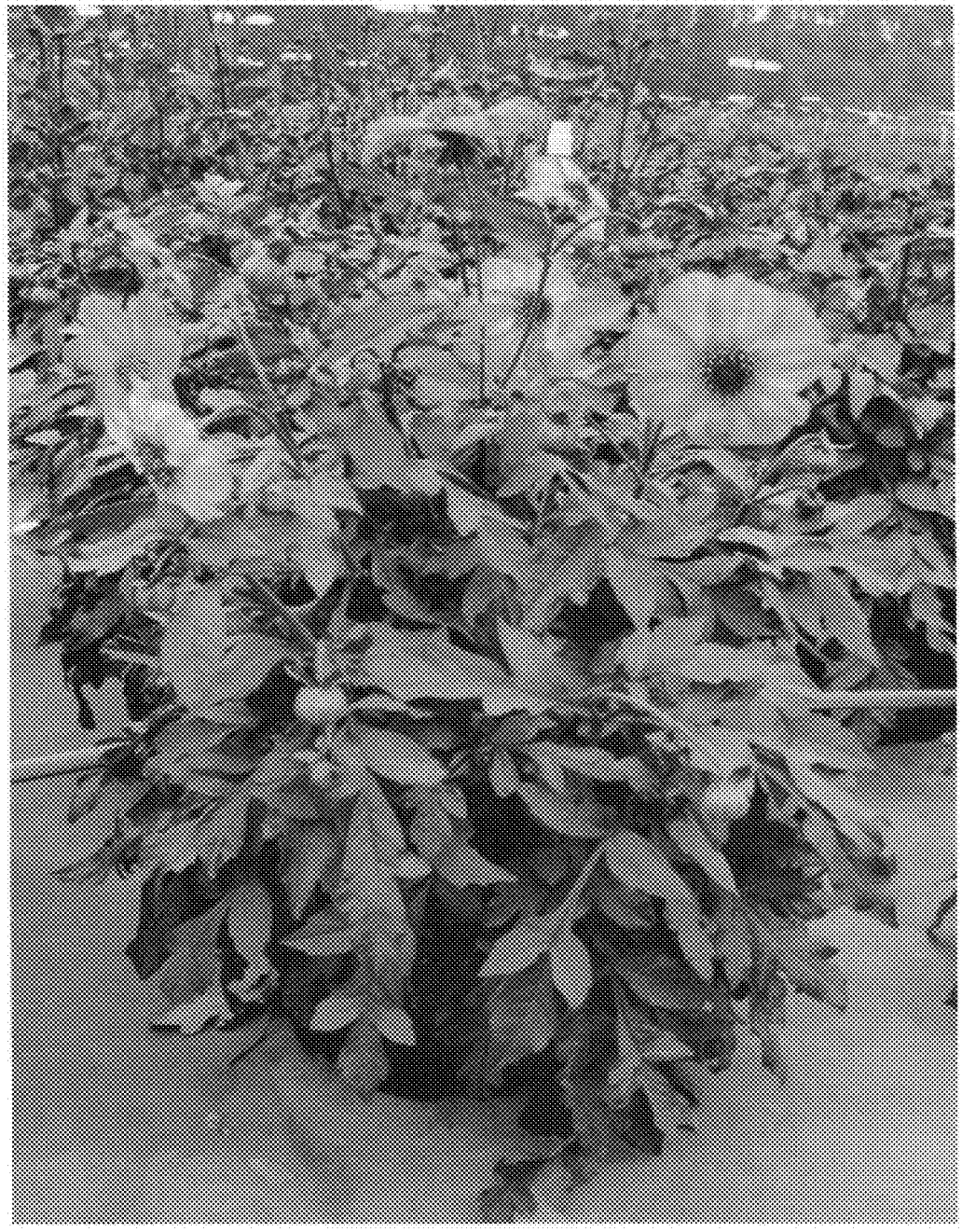

Genus: *DAHLIA*.
Species: *variabilis*.
Denomination: 'MYSTIC HAZE'.

BACKGROUND OF THE INVENTION

This application claims the benefit of priority under 35 U.S.C. 119(e) of U.S. Provisional Application No. 61/455,188 filed on Oct. 18, 2010 entitled *DAHLIA* plant named 'MYSTIC HAZE'.

The present invention relates to a new and distinct cultivar of *Dahlia* grown for use in mixed combinations, beds and the landscape. The new invention is known botanically as *Dahlia variabilis* and will be referred to hereinafter by the cultivar name 'MYSTIC HAZE'. The specific epithet variabilis represents a hybrid seedling line that came from crossing various original wild species in the early 1800's, and refers to the species' wide range of flower color and shapes. *Dahlia* is in the family Compositae. The flower of 'MYSTIC HAZE' is a "single" form blossom and exhibits a single row of ray flowers surrounding a central cluster of disk florets.

'MYSTIC HAZE' was selected as a seedling that resulted from the controlled cross-pollination carried out by the inventor in a cultivated area of Auckland, New Zealand. The breeding began in 1995 by crossing an individual plant *Dahlia variabilis* 'Scarlet Fern' (U.S. Plant Pat. No. 18,989) as the female parent and an individual of *Dahlia variabilis* 'Colour Sucker' (unpatented) as the male parent. Seed was collected from the female parent and coded as 71500/04, then sown with the intention of making a selection from the seedlings that resulted.

'MYSTIC HAZE' was selected in 2004 based on the criteria of leaf color, leaf shape, plant height, and flower color. Selection was conducted by the inventor, in Auckland, New Zealand. The unique traits that distinguish the new *Dahlia* variety named 'MYSTIC HAZE' from other varieties of *Dahlia* known to the inventor are glossy mahogany-black divided leaves and profusions of apricot-orange blossoms with soft yellow inner halo and dark central discs. The new *Dahlia* named 'MYSTIC HAZE' is distinguishable from the parents predominantly by flower color. The flowers of 'Scarlet Fern' are uniformly orange-red in color. The flowers of 'Colour Sucker' are white in color.

'MYSTIC HAZE' exhibits a compact rounded habit, fragrant apricot-orange flowers with a soft yellow halo and dark central discs, glossy mahogany-black foliage, and dark purple-brown stems. The large single blossoms bloom in summer and fall. Cultural conditions include full sun, regular water and rich well-draining potting soil. 'MYSTIC HAZE' is hardy to USDA Zone 9 and grows to 1.2 m in height and 0.9 m in width at maturity.

The first asexual reproduction of 'MYSTIC HAZE' was conducted in 2004 in Auckland, New Zealand. The method of asexual propagation utilized was softwood cuttings from the tuber in year two and tissue culture thereafter. Since that time under careful observation, the distinguishing characteristics have been determined stable, uniform, and to be reproduced true to type in subsequent generations of asexual propagation.

SUMMARY OF THE INVENTION

The following traits have been repeatedly observed and represent the distinguishing characteristics of the new *Dahlia* cultivar named 'MYSTIC HAZE'. These traits in combination distinguish 'MYSTIC HAZE' from all other existing varieties of *Dahlia* known to the inventor. 'MYSTIC HAZE' has not been tested under all possible conditions and phenotypic differences may be observed with variations in environmental, climatic, and cultural conditions, however, without any variance in genotype.

1. 'MYSTIC HAZE' exhibits compact rounded habit.
2. 'MYSTIC HAZE' exhibits glossy mahogany-black divided leaves and dark purple-brown stems.
3. 'MYSTIC HAZE' is grown for use in mixed combinations, beds and the landscape.
4. 'MYSTIC HAZE' exhibits large apricot-orange blossoms with a soft yellow inner halo and dark central discs.
5. 'MYSTIC HAZE' blooms summer and fall.
6. 'MYSTIC HAZE' grows to 1.2 m in height and 0.9 m in width at maturity.
7. 'MYSTIC HAZE' is hardy to USDA Zone 9.

BRIEF DECRIPTION OF THE DRAWINGS

Figure 2:
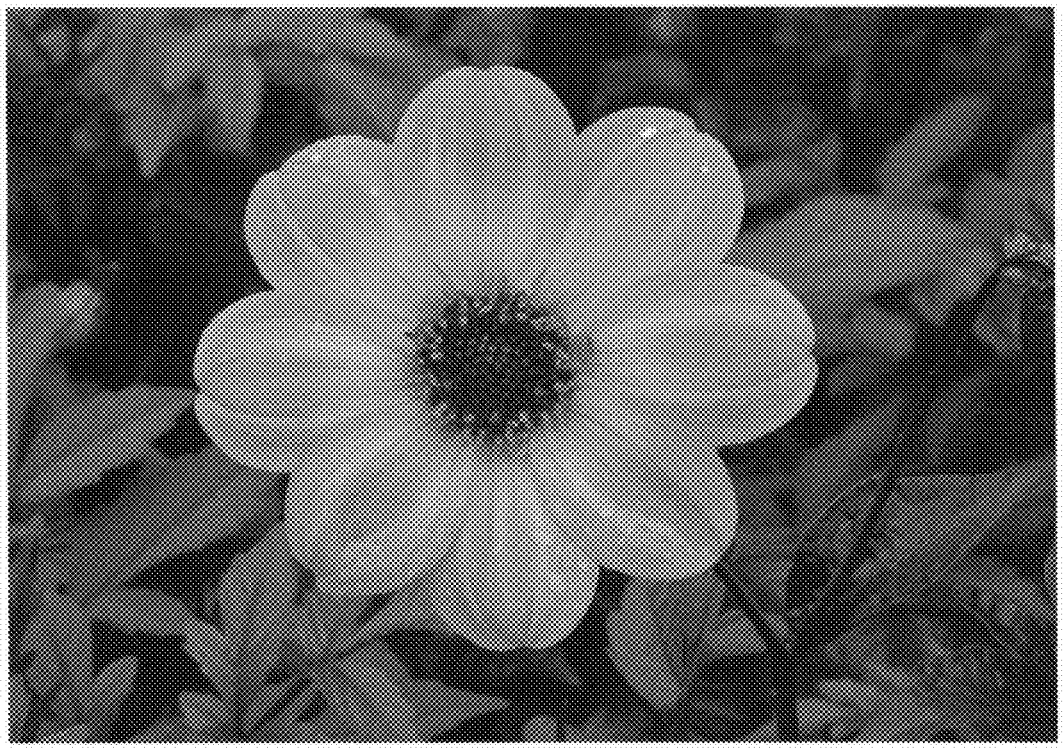

The accompanying color drawings labeled FIG. 1 and FIG. 2 illustrate the overall appearance of the new *Dahlia* cultivar named 'MYSTIC HAZE' showing the colors as true as is reasonably possible to obtain in colored reproductions of this type. Colors in the photographs may differ from the color values cited in the detailed botanical description, which accurately describes the actual colors of the new *Dahlia* variety named 'MYSTIC HAZE'.

The drawing labeled FIG. 1 depicts the entire plant in bloom.

The drawing labeled FIG. 2 depicts a close-up view of a flower.

The drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Dahlia* cultivar named 'MYSTIC HAZE'. Observations, measurements, values and comparisons were collected in Santa Barbara, Calif. from a 9 month old plant grown in the landscape. Color determinations were made in accordance with The 2007 Royal Horticultural Society Colour Chart from London England, except where general color terms of ordinary dictionary significance are used. Growing requirements are similar to the species.

Botanical classification: *Dahlia variabilis* 'MYSTIC HAZE'.

Family: Compositae.

Genus: *DAHLIA*.

Species: *variabilis*.

Denomination: 'MYSTIC HAZE'.

Common name: *Dahlia*.

Parentage: *Dahlia variabilis* 'MYSTIC HAZE' is a seedling that resulted from the controlled cross-pollination of the following parents:

*Female parent.*—*Dahlia variabilis* 'Scarlet Fern' (U.S. Plant Pat. No. 18,989).

*Male parent.*—*Dahlia variabilis* 'Colour Sucker' (unpatented).

Propagation method: Tissue culture.

Rooting system: Fine and fibrous.

Vigor: Vigorous.

Habit: Upright habit.

Use: For use in mixed combinations, beds and the landscape.

Type: Perennial.

Dimensions in first season: 0.6 m in height and 0.6 m in width.

Dimensions at maturity: 1.2 m in height and 0.9 m in width.

Cultural requirements: Grow in full sun with regular water, and well-draining potting soil.

Pest susceptibility: Susceptible to aphids.

Disease susceptibility: Susceptible to mildew in highly humid conditions.

Hardiness: USDA Zone 9.

Stem:

*Color.*—N187A.

*Shape.*—Cylindrical.

*Dimensions.*—50 cm in length 1.5 cm at base, 0.7 cm below uppermost leaf.

*Surface.*—Glabrous.

*Internode length* (*average*).—12 cm.

Foliage:

*Type.*—Evergreen.

*Leaf arrangement.*—Opposite.

*Leaf division.*—Simple.

*Leaf dimensions* (*average*).—10 cm-15 cm in length and 5 cm-6 cm in width.

*Leaf color* (*adaxial surface*).—Ranges between N186A and 200A.

*Leaf color* (*abaxial surface*).—147B.

*Margin.*—Ciliate and pinnatisect.

*Leaf shape.*—Hastate.

*Leaf base.*—Attenuate.

*Leaf apex.*—Apiculate.

*Leaf venation pattern.*—Pinnate.

*Vein color* (*abaxial and adaxial surfaces*).—N137D.

*Vein midrib* (*abaxial surface only*).—Lightly pubescent. Hairs, 1 mm long, fine, light gray.

*Leaf surfaces* (*abaxial surfaces*).—Slightly puberulent.

*Leaf surfaces* (*adaxial surfaces*).—Glabrous.

*Leaf attachment.*—Petiolate.

*Leaf fragrance.*—None observed.

*Petiole shape.*—Sulcate.

*Petiole dimensions.*—0.5 cm to 2 cm in length and 3 mm to 4 mm in width.

*Petiole color.*—N187A.

Inflorescence:

*Inflorescence type.*—Terminal: Flowers classified as "single" form, with single row of ray flowers surrounding a central cluster of disk florets.

*Aspect.*—Facing upward and outward.

*Inflorescence quantity.*—15-20 per 2-litre container plant.

*Dimensions of inflorescence* (*average*).—9.5 cm in diameter and 2.5 cm in depth.

*Inflorescence shape.*—Radiate with center disk.

*Blooming seasons.*—Summer and fall.

*Peduncle.*—Dimensions (average): 20 cm in length and 0.3 cm to 0.4 cm in diameter. Shape: Cylindrical. Surface: Glabrous. Color: N187A.

*Bud.*—Shape: Oblate. Dimensions (average): 1.2 cm in height and 1.5 cm in diameter. Surface: Glabrous. Appearance: Semi-glossy. Color: 153D except 187B at flattened apex immediately prior to opening. Apex: Obtuse. Base: Truncate.

*Ray florets.*—Petals: Quantity per inflorescence: 8-10. Dimensions (average): 4.50 cm in length and 3.2 cm in width. Shape: Obovate. Apex: Obtuse with minute acute tip. Base: Cuneate. Margin: Entire. Surface (adaxial and abaxial): Glabrous. Arrangement: Radiate. Color (adaxial): Petal base N34B; lower (inner) one-third of petal ranges between 3A and 16A giving the effect of an inner halo, fusing into remainder of petal N25D. Color (abaxial): 154A. Vein color (adaxial): N144A.

Vein color (abaxial): Prominently N34B. Vein pattern: Parallel.

*Disk florets.*—Quantity of disk florets: 50-60 per inflorescence. Dimensions: 1.3 cm in length and 1.5 cm in width. Color: Ranges between N35A and 53A. Petals: 8 in number. Petals fused or unfused: Fused. Petal apex: Acute. Petal surface (ventral and dorsal surfaces): Glabrous. Receptacle dimensions: 0.7 cm in depth and 2.5 cm in diameter. Receptacle surface: Glabrous. Receptacle color: 53A.

*Phyllary*.—Inner phyllary: Number: 8. Shape: Elongated ovate. Dimensions: 2.0-2.5 cm in length and 8 mm-11 mm in width. Color (adaxial and abaxial surfaces): 151D except 139C at base. Texture: Scarious, waxy. Appearance: Translucent. Apex: Rounded to subacute. Base: Truncate. Margin: Entire. Surface (adaxial and abaxial): Glabrous. Outer phyllary: Number: 5 in number. Shape: Obovate. Dimensions: 1.50 cm in length and 0.8 cm in width. Color (adaxial and abaxial surfaces): 200A. Form: Reflexed. Apex: Obtuse. Base: Truncate. Margin: Entire. Surface (adaxial): Glabrous, glossy, ribbed. Approximately 10 longitudinal ribs 0.5-0.8 mm apart. Surface (abaxial): Glabrous, glossy, smooth.

*Self-cleaning or persistent*.—Self-cleaning.

*Fragrance of inflorescence*.—Perfumed.

Reproductive organs:

*Stamens*.—5 in number.

*Stamen attachment*.—Filament adnate to ventral surface of corolla.

*Stamen length*.—6 mm in length.

*Stamen color*.—169A.

*Anther*.—Connate.

*Anther color*.—169A.

*Pollen*.—Present.

*Quantity*.—Large amount.

*Pollen color*.—17A.

*Pistil*.—One present.

*Pistil length*.—12 mm in length.

*Stigma dimensions*.—3 mm in length and 0.5 mm in width.

*Stigma form*.—Plumose.

*Stigma color*.—N169A.

*Stigma shape*.—Bifurcate.

*Ovary position*.—Inferior.

*Ovary color*.—150D.

*Ovary shape*.—Rotund.

*Ovary dimensions*.—2 mm in width and 3 mm in height.

Seed: None observed to date.

The invention claimed is:

1. A new and distinct cultivar of *Dahlia* plant named 'MYSTIC HAZE' as described and illustrated herein.

* * * * *